United States Patent [19]
Ash et al.

[11] Patent Number: 6,042,561
[45] Date of Patent: Mar. 28, 2000

[54] NON-INTRAVASCULAR INFUSION ACCESS DEVICE

[75] Inventors: Stephen R. Ash, Lafayette; Elsa M. Janle, West Lafayette, both of Ind.

[73] Assignee: Ash Medical Systems, Inc., West Lafayette, Ind.

[21] Appl. No.: 08/956,001

[22] Filed: Oct. 22, 1997

[51] Int. Cl.[7] .............................. A61M 11/00; A61K 9/22
[52] U.S. Cl. .......................................... 604/93; 604/890.1
[58] Field of Search ................................ 604/93, 19, 29, 604/27, 28, 30, 51–53, 118, 264, 158, 161, 174, 175, 280, 890.1, 891.1

[56] References Cited

U.S. PATENT DOCUMENTS

| | | | |
|---|---|---|---|
| 3,064,653 | 11/1962 | Coanda | 604/49 |
| 3,633,585 | 1/1972 | McDonald, Jr. | 604/29 |
| 4,209,014 | 6/1980 | Sefton | 128/214 F |
| 4,351,333 | 9/1982 | Lazarus et al. | 128/214.4 |
| 4,364,385 | 12/1982 | Lossef | 604/890.1 |
| 4,402,694 | 9/1983 | Ash et al. | 604/891 |
| 4,479,792 | 10/1984 | Lazarus et al. | 604/29 |
| 4,605,399 | 8/1986 | Weston et al. | 604/305 |
| 4,687,471 | 8/1987 | Twardowski et al. | 604/175 |
| 4,726,381 | 2/1988 | Jones | 128/632 |
| 4,753,636 | 6/1988 | Free | 604/49 |
| 4,772,269 | 9/1988 | Twardowski et al. | 604/175 |
| 4,777,953 | 10/1988 | Ash et al. | 128/635 |
| 4,854,322 | 8/1989 | Ash et al. | 128/635 |
| 4,935,004 | 6/1990 | Cruz | 604/29 |
| 5,057,075 | 10/1991 | Moncrief et al. | 604/49 |
| 5,098,413 | 3/1992 | Trudell et al. | 604/281 |
| 5,254,084 | 10/1993 | Geary | 604/29 |
| 5,549,603 | 8/1996 | Feiring | 604/21 |
| 5,593,384 | 1/1997 | Halem | 604/93 |
| 5,713,858 | 2/1998 | Heruth et al. | 604/93 |
| 5,752,939 | 5/1998 | Makoto | 604/175 |
| 5,776,111 | 7/1998 | Tesio | 604/264 |
| 5,807,315 | 9/1998 | Van Antwerp et al. | 604/49 |

*Primary Examiner*—Wynn Wood Coggins
*Assistant Examiner*—Sharon Finkel
*Attorney, Agent, or Firm*—Woodard, Emhardt, Naughton Moriarty & McNett Patent and Trademark Attorneys

[57] ABSTRACT

A non-intravascular infusion access device and method for long-term continuous infusion of drugs. The infusion access device includes a porous membrane made of a material which is biocompatible for long-term patency inside the body. The porous membrane is connected to a conducting tubing which exits from the body and is connected to a drug infusion system. At the exit site is a cuff of porous material. The cuff serves to anchor the access device in position as the surrounding body tissue grows back around the cuff. There are also two small suture retainers for stabilizing the position of the access device relative until tissue ingrowth occurs in and around the cuff.

16 Claims, 5 Drawing Sheets

NON-INTRAVASCULAR INFUSION ACCESS DEVICE

BACKGROUND OF THE INVENTION

The present invention relates generally to the field of medical devices and methods and, more particularly, to a device and method for infusion of therapeutic agents into the body.

Six million Americans have diabetes. There are two major types of diabetes, Type I (Insulin Dependent Diabetes) and Type II (Insulin Independent Diabetes). About 80% of the diabetics are Type II and about 20% are Type I. All of the Type I diabetics require insulin treatment and many of the Type II patients also require insulin.

In order to achieve good glucose control the insulin administration must be matched to the blood glucose availability. Blood glucose levels are influenced by food intake, exercise, stress and illness. It has become evident that by matching the insulin dosage to glucose intake and achieving good glucose control the long-term complications of diabetes can be diminished. In 1986 the cost of treatment of diabetic complications was $16 billion dollars or 4% of the federal budget. These long-term complications of diabetes include renal failure, cardiovascular disease, blindness and amputations. Continuous insulin infusion using portable infusion pumps has become an important method of treating insulin dependent diabetics. In 1985, there were about 10,000 insulin pumps in use. The use of pumps to deliver insulin has a number of advantages over the more widely used method of insulin injections. Most insulin pumps in use today are small in size, about as large as a deck of cards. The primary advantage in using such pumps for insulin administration is that insulin can be delivered at a slow, basal rate, continuously and at a higher rate after food consumption. This pattern of insulin administration mimics more closely the normal secretion pattern of the human pancreas than does the insulin absorption from injected insulin. Another advantage is that the rate can be varied to meet changing demands and unplanned events, such as a change in meal time or size, can be compensated for easily. To even begin to approach the insulin patterns achievable by insulin infusion pumps using injections requires at least 4 injections per day. Because continuous infusion of a drug offers the advantages of maintaining more constant drug levels than by bolus administration, swings in concentration depending on the absorption and elimination characteristics of the drug can be compensated for more easily. Maintaining a constant low level of a drug becomes especially important in drugs which must have a certain minimum concentration level in the body to be effective but become toxic at higher levels. Bolus administration of drugs with a low therapeutic index may expose patients to transient toxic levels of a drug to maintain the necessary effective lower level. Availability of a more permanent access device provides the option of infusing a greater variety of drugs to maintain constant low effective concentration while minimizing the exposure of the patient to toxic levels of a particular drug. Examples of these types of drugs for which this feature would be useful include chemotherapy agents used to treat cancer and immunosuppressive drugs used to prevent post-transplant tissue rejection.

One example of a continuous insulin infusion pump contains an insulin reservoir which is connected to a long tube having a needle at the opposite end. The needle is inserted into the subcutaneous tissue, usually the abdomen, and taped in place. There are several problems associated with this method, which is generally known as the subcutaneous access method. First, the mere presence of the needle can be painful. Any bumps or abrasions to the area of the needle insertion cause additional pain. Since the needle is secured in place only by tape, there is the possibility that it will become dislodged without the patient even being aware of the dislodgement. This can result in the patient not receiving the needed medication. For diabetics whose insulin is not being administered, such an occurrence can lead to ketoacidosis and coma.

In addition, some people are allergic to the tapes used to hold the needle in place. Yet further, certain patients are prone to infection of the needle insertion sites. This may be due to a lowered resistance to infection or to poor insertion procedures. Unfortunately, such infections are not uncommon. As an example, in one study lasting 1½ years 29% of the patients involved developed an infection serious enough to require antibiotic therapy.

As an alternative to the subcutaneous needle, a catheter like device consisting of a short plastic tube having a needle stylus inside can be employed. The catheter/needle combination is inserted into the tissue and the needle removed, thereby leaving the catheter in place. An advantage of a catheter over a hollow needle is that a catheter is less painful in place and more body compatible. However, whether the access device for the external pump is a hollow needle or catheter/needle combination, they can be left in place for only a few days before a new needle or catheter must be inserted because of the risk of infection entering the body through the open lumen or around the exterior surface of the device. Also, with either the hollow needle or catheter/needle combination, absorption of the therapeutic agent is limited due to the limited body area contiguous to the lumen opening. This is not a significant problem in vasculr infusion situations because of the ability of the bloodstream to carry and diffuse the therapeutic agent throughout the body. Moreover, many of the other above-described disadvantages associated with the hollow needle are still present when a catheter is used as a the access device.

In addition to external mounted infusion pumps, there are also permanently implantable infusion pumps. Characteristically, such pumps contain reservoirs for insulin which must be filled periodically from outside the body by injecting insulin into the reservoir through a septum which is placed near the skin surface. So far, these devices have been used only on an experimental basis. There are at least several potential disadvantages in an infusion system of this type. For example, in the case of a malfunction, major surgery would be required to remove the pump. There is also the risk of a malfunction of the type which would cause a "run away pump." As opposed to an external pump which can be simply disconnected by the patient or a family member, it would require a trained professional to stop a malfunctioning implanted infusion pump. Further, changing the operational programming in an implantable pump is inherently more complicated than an external mounted pump because it must be done remotely. Of added concern are the infections which can occur in the body area or pocket formed around the pump. The onset of such infections usually necessitates removal of the pump. Moreover, if the catheter leading from the pump is placed inside the vascular system there is the undesired potential of decreased flow rate due to thrombus formation at the end of the catheter.

SUMMARY OF THE INVENTION

A non-intravascular infusion access device for long-term continuous infusion of drugs according to one embodiment of the present invention includes a porous membrane made of a material which is biocompatible for long-term patency inside the body. The porous membrane is connected to a conducting tubing which exits from the body and is connected to a drug infusion system. At the body exit site is a cuff of porous material which serves to anchor the access device in position when tissue ingrowth into the cuff has occurred. There are also two small suture retainers for anchoring the access device with a suture until there is sufficient tissue ingrowth in the cuff to stabilize the position of the device.

The present invention also comprises a method for continuous long-term infusion of a drug into a non-intravascular access site.

It is an object of the present invention to provide an improved method and device for continuous drug infusion into a non-intravascular location.

It is a further object of the present invention to provide an improved method and device for continuous drug infusion into a non-intravascular location which increases comfort to the patient and decreases the possibility of the access device becoming dislodged.

It is a yet further object of the present invention to provide an improved method and device for continuous drug infusion into a non-intravascular location which infuses the drug over an increased surface area thereby providing faster absorption of the drug in the body.

It is an additional object of the present invention to provide an improved method and device for continuous drug infusion into a non-intravascular location which decreases the risk of infection when used over long periods.

It is an additional object of the present invention to provide an improved method and device for continuous drug infusion which is useful for insulin infusion into subcutaneous tissues and which is also suitable for infusion of other drugs in subcutaneous tissues and other non-intravascular locations, such as tumor tissues in cancer drug therapy.

Related objects and advantages of the present invention will become more apparent by reference to the following figures and detailed description.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
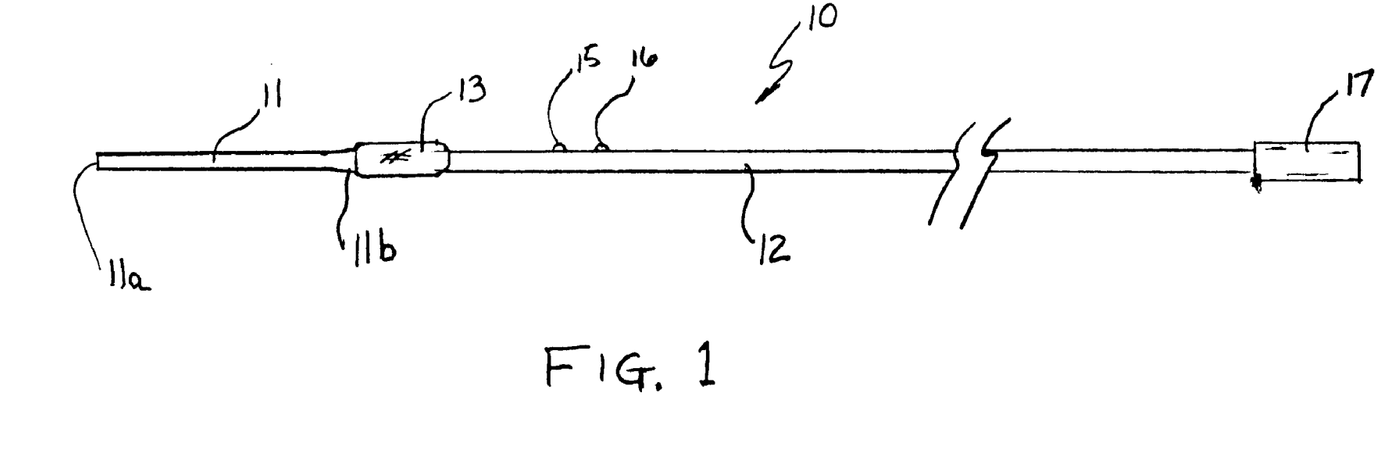
FIG. 1 is an elevation view of the infusion access device of the present invention.
Figure 2:
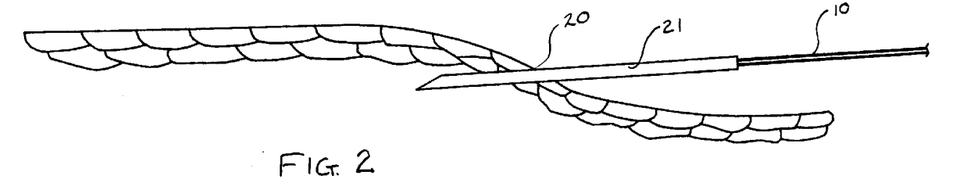
FIGS. 2–6 depict successive steps in the implantation of the infusion access device of the present invention in a subcutaneous body location.

Referring to FIG. 1, a preferred embodiment of the infusion access device of the present invention is shown generally at 10. In this embodiment, the device 10 is specifically designed to administer the infusion of insulin into a subcutaneous body location. Nevertheless, it will be appreciated by those skilled in the art that the device 10 can be modified to permit the infusion of other types of therapeutic agents and to permit access to other non-intravascular body locations.

At the distal or body end of the device 10 is a generally elongate tubular shaped porous membrane 11. The porous membrane 11 acts as a filter to allow free flow of the drug molecules being infused therethrough, in this case insulin, while preventing larger bacteria or viruses from entering the body. Membrane 11 is sized such that the area of its outer surface exposed to the body is substantially larger, e.g., preferably at least several times larger, than the cross-sectional area of the lumen at the open end of conducting tubing 12 which extends into the body. Thus, membrane 11 also serves to significantly increase the surface area over which the drug is infused into and absorbed by the body. In the preferred embodiment used for insulin infusion, the membrane 11 has a length of about 0.78 inches, an outer diameter of about 0.04 inches and is formed of a copolymer of polyacrylonitrile and polyvinylchloride manufactured by W. R. Grace, Lexington, Mass. with the diameter of the membrane pores sized to allow the free passage of insulin molecules up to about 50,000 daltons in molecular weight.

It should be understood, however, that the pore size of membrane 11 may be increased or decreased, or its filtering characteristics otherwise changed, depending upon the type of drug or drugs being infused. This may be accomplished in a variety of ways known to those skilled in the art, such as by changing the membrane material composition, thickness, etc. Since in all cases it will be desirable to limit the risk of infection or disease being carried into the body through the device, the pore size of the membrane should minimally have a cutoff no greater than about 0.2 to 1 micron diameter. At the lower end of this range, i.e., about 0.2 microns, the passage of all bacteria and most types of viruses will be restricted, while a 1 micron cutoff will at least restrict the passage of bacteria.

The porous membrane 11 has a closed end 11a and an open end 11b. The open end 11b of the porous membrane 11 is inserted over an end of a length of flexible conducting tubing 12 and affixed thereto by a suitable biocompatible adhesive such as Dymax medical grade ultraviolet curing adhesive. The conducting tubing 12 is adapted to extend externally of the body with the porous membrane 11 implanted subcutaneously.

At the junction of the membrane and the conducting tubing is a porous cuff 13. The purpose of cuff 13 is to allow tissue ingrowth into the cuff and seal off any path for passage of skin bacteria around the device, and also to serve as an anchoring means to anchor the device in the body after sutures are removed. Cuff 13 is preferably made of expanded polytetrafluoroethylene, although other porous materials which promote ingrowth of fibroblast and fibrous tissue, such as Dacron or textured polyurethane may also be employed. As with the membrane 11, cuff 13 is secured to conducting tubing 12 by a suitable adhesive.

In the embodiment shown, the conducting tubing 12 has a 0.025" inside diameter and 0.040" outside diameter.

Further, although other materials may alternatively be used for the conducting tubing 12, it has been found that polyurethane tubing bonds well to the expanded polytetrafluoroethylene cuff 13 and membrane 12 while also possessing good biocompatibility and flexibility characteristics.

Located on and protruding from the exterior surface of the conducting tubing 12 approximately one half inch proximal of the cuff 13 are two small ovular shaped suture retainers 15 and 16. Suture retainers 15 and 16 are axially aligned along the length of the tubing 12 and are spaced approximately ⅛ inch apart. In the preferred embodiment shown, the suture retainers 15 and 16 are formed from droplets of Dymax medical grade ultraviolet curing adhesive.

Figure 5:
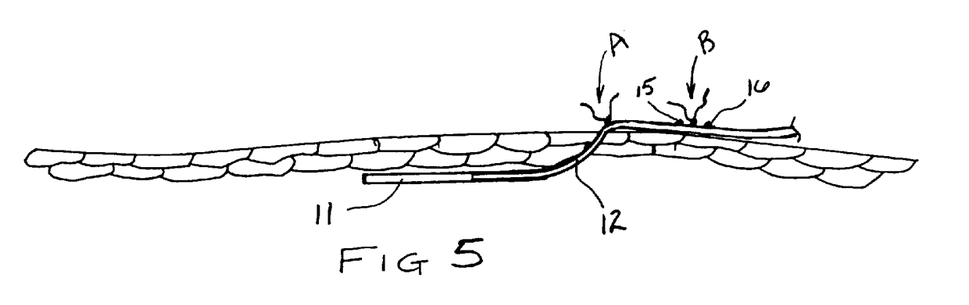

At the proximal end of the conducting tubing 12 is an adapter 17 which serves to permit connection and disconnection of the device 10 with an infusion pump 23, shown diagrammatically in FIG. 5. The adapter 17 is formed of a length of small gauge tubing made from steel or other suitably rigid metal.

While it is preferred for reasons previously mentioned that the pump 19 be positioned externally of the body, the device 10 can also be used with implantable infusion pumps. The pump 19 may be a conventionally known pump, such as for example a CPI Betatron II insulin infusion pump manufactured by CPI/Lilly located in St. Paul, Minn.

Referring to FIGS. 2–6, the preferred method of placement of the infusion access device 10 into a suitable subcutaneous body location will now be described. First, the tissue in the area of the body entrance site 20 is anesthetized with a local anesthetic. The distal portion of the subcutaneous infusion access device 10 including the porous membrane 11 is placed inside the lumen of an introducer 21 in the form of a rigid hollow needle. Of course, the outside diameter of the membrane 11 and conducting tubing 12 are sized to allow them to slide freely inside the introducer 21. In the embodiment shown, the hollow needle introducer is a 13 gauge size and made of stainless steel.

Preferably, the device 10 and introducer 21 can be conveniently provided to the physician in a sterile, prepackaged kit intended for one-time use.

Figure 3:
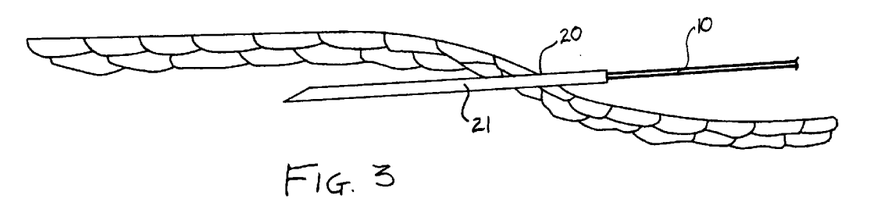
Figure 4:
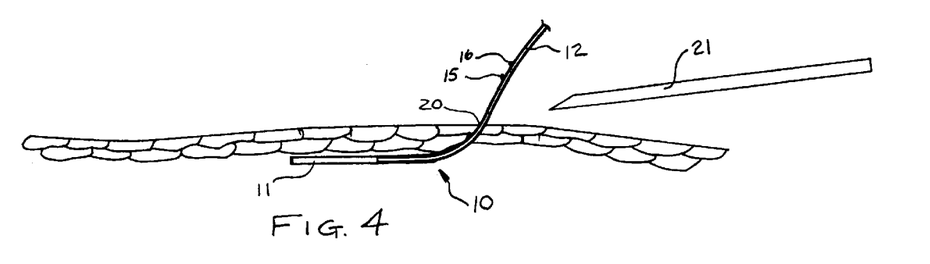

A small stab incision is made in the anesthetized skin. The introducer 21 is inserted through the incision (FIG. 2) and advanced sufficiently beneath the skin so that the membrane 11 will be totally implanted within the subcutaneous area when the introducer is withdrawn (FIG. 3). The introducer is then withdrawn (FIG. 4) while the device 10 is held in place, leaving the membrane 11 under the skin. A skin suture "A" is made around the device at the entrance site, closing the incision. Another suture "B" is then placed around the device between the suture retainers 15 and 16 (FIG. 5). This additional suture serves to further stabilize the device and prevent accidental withdrawal from the body. Both of the sutures can be removed after the position of the device 10 is stabilized in the body by fibrous tissue ingrowth into the cuff 13. Once the patency of the device 10 is confirmed, infusion of insulin from container 22 into the body can be started by activation of infusion pump 23 (FIG. 6).

Figure 6:
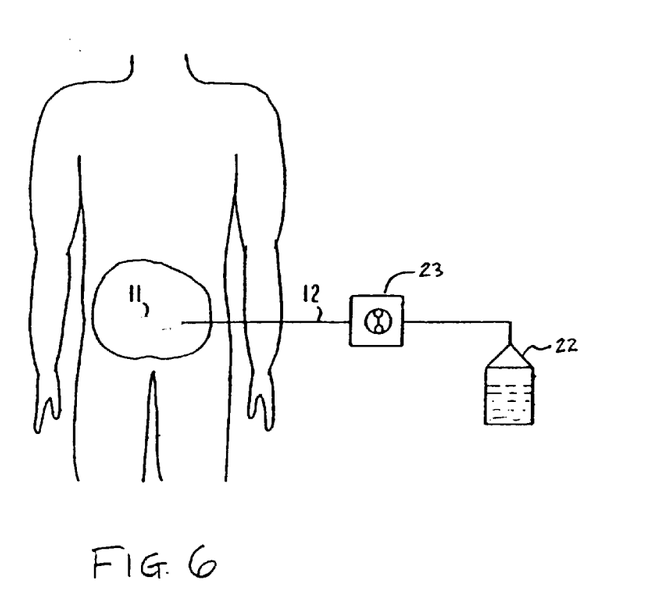

FIG. 6 diagrammatically shows placement of the device 10 in the subcutaneous tissue of the abdomen. Other possible locations for insulin administration are the peritoneal cavity or an intramuscular location.

Figure 7:
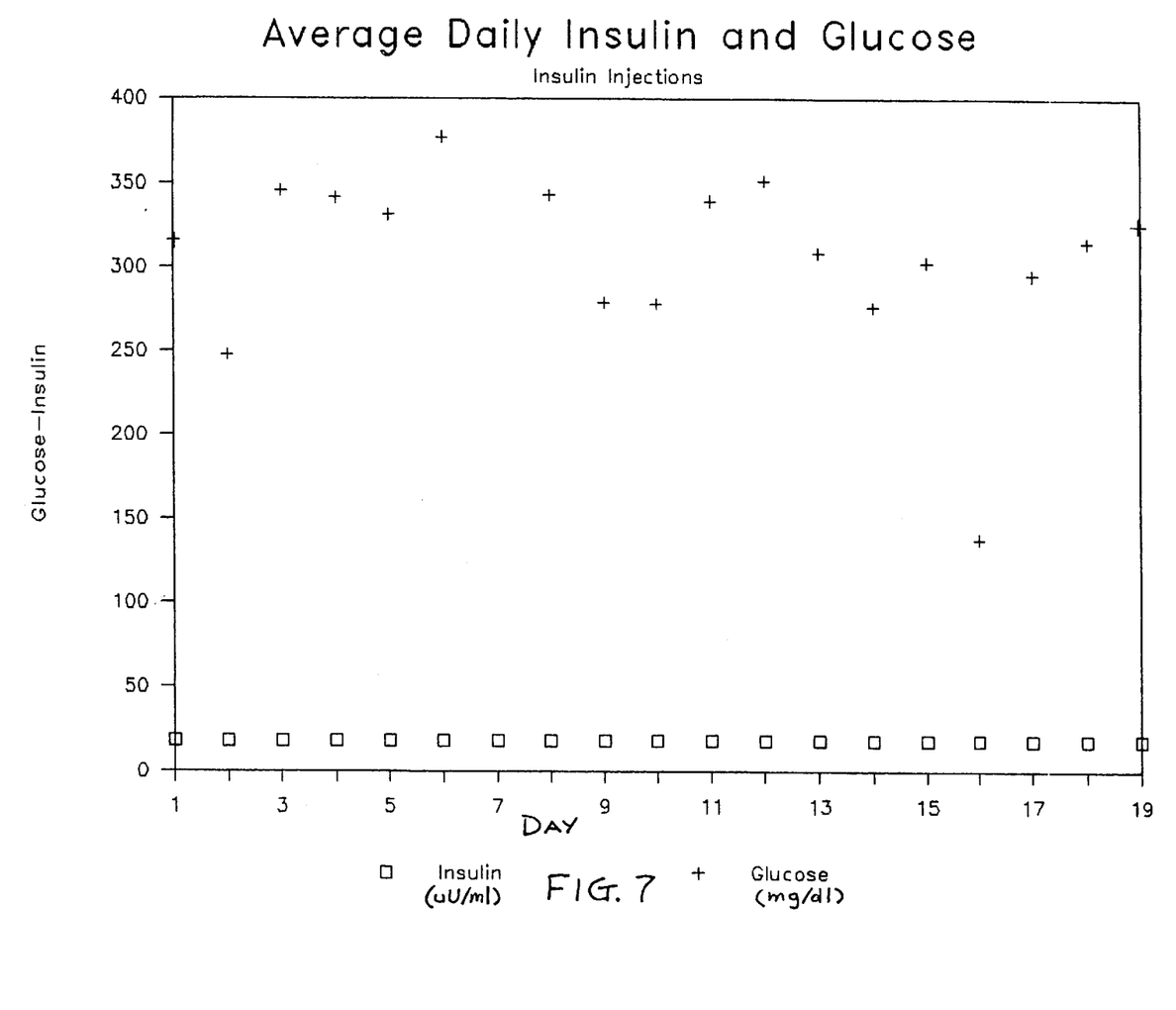
FIG. 7 is a graph of test results showing the insulin dosage and glucose response for a test dog being administered insulin by the conventional subcutaneous injection method.
Figure 8:
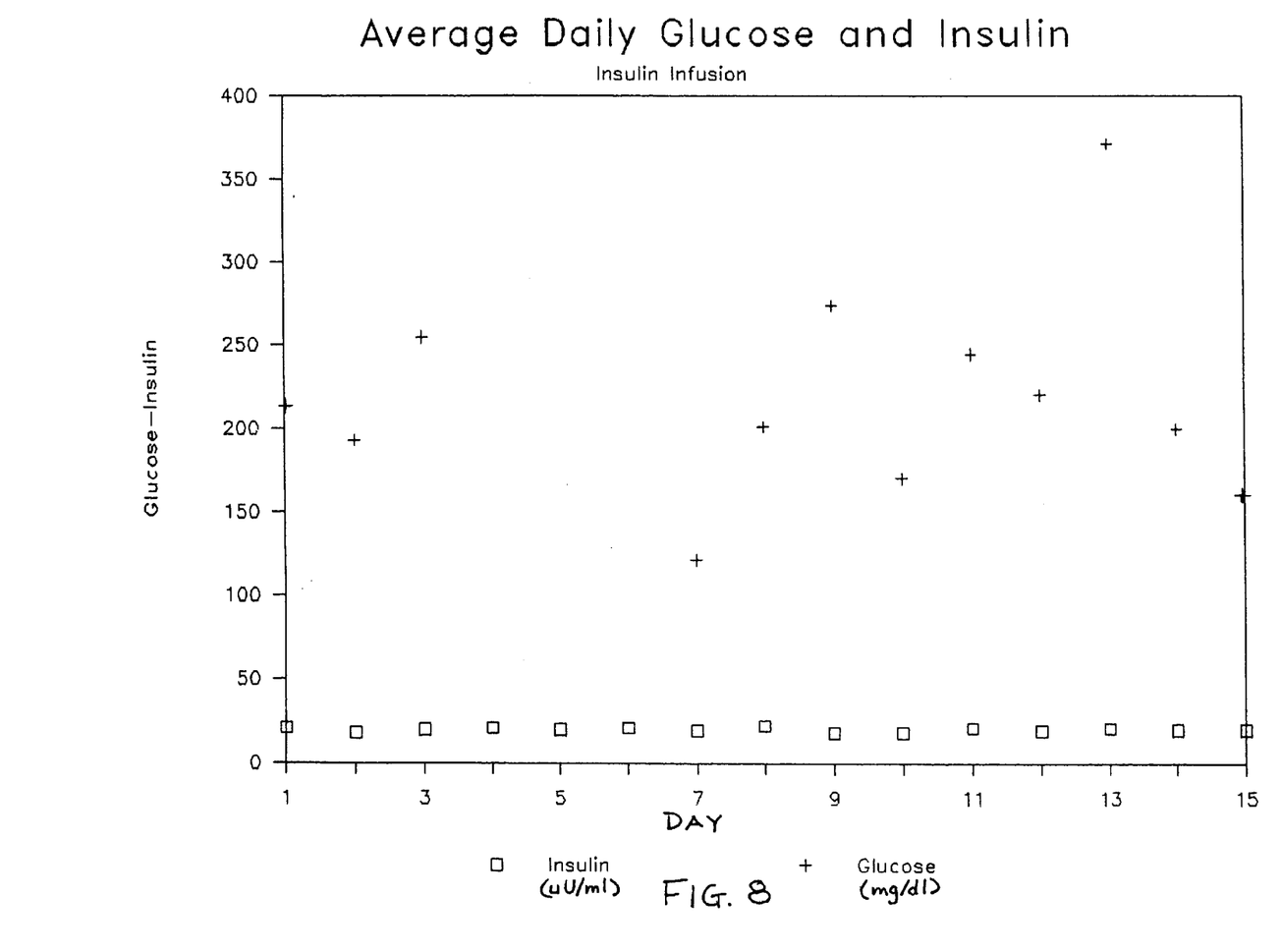
FIG. 8 is a graph of test results showing the insulation dosage and glucose response for the same test dog used to obtain the results shown in FIG. 7 using the infusion access device of the present invention to provide continuous insulin infusion.

The results of a comparison study between the device 10 of the present invention and conventional injection administration is illustrated in FIGS. 7 and 8. The results graphed in FIG. 7 were obtained in a subject test dog by administering insulin injections of Regular and NPH insulins two times per day. The total daily insulin dosage administered by such injections was 18 units. The FIG. 7 graph depicts the change in blood glucose levels over time, with the "+" representing average daily blood glucose levels (mg/dl) and the square symbol indicating the amount of insulin (uU/ml) administered each day.

As FIG. 7 shows, the average daily glucose levels of the test dog fluctuated greatly and were frequently above the desired maximum 250 mg/dl level. The graph of FIG. 8 shows the insulin infusion and glucose levels for the same test dog, but wherein insulin was received solely by infusion through the infusion access device of the present invention. In this test, insulin was infused into the test dog at a constant basal insulin infusion rate on a continuous "around the clock" basis supplemented by bolus doses of insulin given with meals. As in FIG. 7, the "+" represents average daily blood glucose levels (mg/dl) and the square symbols indicate the amount of insulin (uU/ml) administered each day. As can be seen by comparing the graphs of FIGS. 7 and 8, there are more glucose levels below the desired maximum 250 mg/dl level with the infusion method than with the injected method.

One major concern for the use of an insulin infusion device when used over prolonged periods, i.e., more than several days, is that insulin sensitivity will decrease over time. Below is a table of the daily total amounts of insulin administered to the test dog over a 14-day period in the FIG. 8 study. As the table and FIGS. 8 show, the insulin sensitivity does not decrease with time. The average dosage over the 14-day period in the FIG. 8 study is only slightly higher than the 18 units/day dosage given by injection to the same test dog in the FIG. 7 study and is reflected in lower average glucose levels.

| Day | Total Insulin Units Infused |
| --- | --- |
| 2 | 16.8 |
| 3 | 18 |
| 4 | 20 |
| 5 | 21 |
| 6 | 19.5 |
| 7 | 21 |
| 8 | 19.5 |
| 9 | 23 |
| 10 | 17.5 |
| 11 | 19 |
| 12 | 21.5 |
| 13 | 20 |
| 14 | 21 |
| 15 | 20 |

While the invention has been illustrated and described in detail in the drawings and foregoing description, the same is to be considered as illustrated and not restrictive in character, it being understood that only the preferred embodiment has been shown and described and that all changes and modifications that come within the spirit of the invention are desired to be protected. Thus for example, while the embodiment shown is especially suited for insulin infusion purposes, the invention can also be used to infuse other drugs in subcutaneous as well as other non-intravascular body locations.

What is claimed is:

1. A non-intravascular infusion access device for long-term continuous infusion of a therapeutic agent into the body, comprising:

an elongate tubular porous membrane having a closed end and an open end, said membrane made of a substantially nonexpandable biocompatible material suitable for implantation within a non-intravascular location inside the body and having pores sized to allow the passage of the therapeutic agent through said membrane while preventing the passage of a member selected from the group consisting of bacteria and viruses;

a conducting tubing having first and second open ends, said conducting tubing sized to permit infusion therethrough of a fluid containing the therapeutic agent, said open end of said tubular porous membrane attached to and in fluid communication with said first open end of said tubing whereby fluid infused through said conducting tubing is caused to flow through said porous membrane;

an infusion delivery system including a fluid source containing the therapeutic agent; and a means for connecting the second open end of said conducting tubing to the infusion delivery system.

2. The non-intravascular infusion access device of claim 1 and further comprising:

a porous cuff extending around said conducting tubing, said cuff being formed of a material compatible with body tissues thereby promoting tissue ingrowth therein when said cuff is implanted within the body.

3. The non-intravascular infusion access device of claim 2 and further comprising a suture retainer means extending from said conducting tubing and adapted to secure the position of said membrane inside the body until the position of said cuff is secured by tissue ingrowth.

4. The non-intravascular infusion access device of claim 3 wherein said suture retainer means includes a pair of ovular shaped suture retainers spaced apart along and protruding from the exterior surface of the conducting tube.

5. The non-intravascular infusion access device of claim 1 wherein the maximum diameter size of the pores in said porous membrane is in the range of about 0.2 to about 1 micron.

6. The non-intravascular infusion access device of claim 1 wherein said porous membrane has pores sized to pass insulin molecules having a molecular weight of up to about 50,000 daltons.

7. The non-intravascular infusion access device of claim 1 wherein said porous membrane has an outer surface area which is greater than the cross-sectional area of said first open end of said conducting tubing.

8. The non-intravascular infusion access device of clam 1 wherein said porous membrane is formed of a copolymer of polyacrylonitrile and polyvinyl chloride.

9. A kit for providing long-term continuous infusion of a therapeutic agent into a non-intravascular body location, comprising:

(a) an elongate tubular porous membrane having a closed end and an open end, said membrane made of a substantially nonexpandable biocompatible material suitable for implantation within a non-intravascular location inside the body and having pores sized to allow the passage of the therapeutic agent through said membrane while preventing the passage of a member selected from the group consisting of bacteria and viruses;

(b) a conducting tubing having one end connected in fluid communication with said open end of said porous membrane and sized to permit infusion therethrough of a fluid containing the therapeutic agent;

(c) an infusion system including a fluid source containing the therapeutic agent configured for connection to said conducting tubing opposite said one end; and (d) an introducer having a passageway sized to slidably receive therethrough at least that portion of said non-intravascular infusion access device including said porous membrane.

10. The kit of claim 9 and further comprising:

a porous cuff extending around said conducting tubing and made from a body compatible material promoting tissue ingrowth.

11. An infusion access device for long-term continuous infusion of insulin into a subcutaneous space within the body, comprising:

an elongate tubular porous membrane having a closed distal and open proximal end, said porous membrane formed of a material compatible for implantation within a subcutaneous body space and having pores sized to allow the passage of insulin through said membrane;

a conducting tubing having one end connected to the proximal open end of said porous membrane in fluid communication therethrough, said conducting tubing sized to permit infusion therethrough of a fluid containing the therapeutic agent; and an adaptor connecting said proximal open end of said conducting tubing to an insulin infusion system.

12. A method for continuous long-term infusion of a therapeutic agent into the body, comprising the acts of:

providing an infusion access device including an elongate tubular porous membrane and a fluid conducting tube;

implanting said porous membrane into a non-intravascular body location;

connecting said infusion access device to an externally located fluid source containing a therapeutic agent whereby the source is in fluid communication with the fluid conducting tube; and infusing a fluid containing the therapeutic agent from said fluid source through said porous membrane;

wherein the elongate tubular porous membrane has a closed end and an open end, said membrane made of a substantially nonexpandable biocompatible material suitable for implantation within a non-intravascular location inside the body and having pores sized to allow the passage of the therapeutic agent through said membrane while preventing the passage of a member selected from the group consisting of bacteria and viruses; and wherein the conducting tubing has first and second open ends, said conducting tubing sized to permit infusion therethrough of a fluid containing the therapeutic agent, said open end of said tubular porous membrane attached to and in fluid communication with said first open end of said tubing whereby fluid infused through said conducting tubing is caused to flow through said porous membrane.

13. The method of claim 12 wherein said implanting is accomplished by using a hollow introducer needle sized to receive therein said porous membrane and said method further comprises:

positioning the porous membrane within said hollow introducer needle;

advancing said hollow introducer needle into a subcutaneous body location; and withdrawing said needle from the body after said porous membrane is desirably positioned within the subcutaneous body location.

14. The method of claim 13 and further comprising:

securing the position of said infusion access device relative to the body.

15. The method of claim 14 wherein said securing is accomplished by applying a skin suture around said conducting tube.

16. The method of claim 15 wherein said infusion access device includes a cuff positioned around said conducting tube and said securing is further accomplished by implanting said cuff into body tissues and allowing ingrowth of said tissues into said cuff.

* * * * *